United States Patent [19]
Safta

[11] Patent Number: 5,376,281
[45] Date of Patent: Dec. 27, 1994

[54] WATER PURIFICATION SYSTEM

[76] Inventor: Eugen Safta, P.O. Box 24041, Winston-Salem, N.C. 27114

[21] Appl. No.: 95,293

[22] Filed: Jul. 21, 1993

[51] Int. Cl.$^5$ ............ C02F 1/32; C02F 1/34; C02F 1/78
[52] U.S. Cl. ............ 210/748; 210/760; 210/764; 210/192; 210/259; 210/900; 422/24
[58] Field of Search ............ 210/900, 192, 259, 748, 210/764, 266, 760; 422/24; 426/66; 423/580

[56] References Cited

U.S. PATENT DOCUMENTS

| | | | |
|---|---|---|---|
| 2,384,778 | 9/1945 | Whitman | 250/436 |
| 3,276,458 | 10/1966 | Iversen et al. | 210/900 |
| 3,837,800 | 9/1974 | Wood | 250/436 |
| 3,870,033 | 2/1975 | Faylor et al. | 165/168 |
| 4,141,830 | 2/1979 | Last | 210/192 |
| 4,160,727 | 7/1979 | Harris, Jr. | 210/900 |
| 4,179,616 | 12/1979 | Coviello et al. | 250/527 |
| 4,189,363 | 2/1980 | Beitzel | 250/527 |
| 4,309,992 | 1/1982 | Dodak et al. | 210/266 |
| 4,548,716 | 10/1985 | Boeve | 210/760 |
| 4,595,500 | 6/1986 | Galbiati | 210/266 |
| 4,661,264 | 4/1987 | Goudy, Jr. | 210/748 |
| 4,664,793 | 5/1987 | Murakami et al. | 210/181 |
| 4,780,287 | 10/1988 | Zeff et al. | 422/186.3 |
| 4,784,772 | 11/1988 | Gotoh et al. | 210/638 |
| 4,788,038 | 11/1988 | Matsunaga | 422/22 |
| 4,798,702 | 1/1989 | Tucker | 420/24 |
| 4,798,847 | 1/1989 | Roesink et al. | 521/901 |
| 4,808,287 | 2/1989 | Hark | 204/182.5 |
| 4,816,145 | 3/1989 | Goudy, Jr. | 422/186.3 |
| 4,842,723 | 6/1989 | Parks et al. | 210/202 |
| 4,851,122 | 7/1989 | Stanley | 210/501 |
| 4,857,204 | 8/1989 | Joklik | 210/695 |
| 4,861,484 | 8/1989 | Lichtin et al. | 210/638 |
| 4,863,608 | 9/1989 | Kawai et al. | 210/638 |
| 4,876,014 | 10/1989 | Malson | 210/668 |
| 4,879,041 | 11/1989 | Kurokawa et al. | 210/640 |
| 4,909,931 | 3/1990 | Bibi | 210/192 |
| 4,990,260 | 2/1991 | Pisani | 210/664 |
| 5,019,256 | 5/1991 | Ifill et al. | 210/232 |
| 5,024,766 | 6/1991 | Mahmud | 210/900 |
| 5,053,143 | 10/1991 | Miller et al. | 210/748 |
| 5,061,374 | 10/1991 | Lewis | 210/266 |
| 5,064,534 | 11/1991 | Busch et al. | 210/266 |
| 5,073,268 | 12/1991 | Saito et al. | 210/638 |
| 5,078,876 | 1/1992 | Whittier et al. | 210/315 |
| 5,098,582 | 3/1992 | Antelman | 210/765 |
| 5,104,546 | 4/1992 | Filson et al. | 210/650 |
| 5,106,503 | 4/1992 | Ohmi et al. | 210/541 |
| 5,114,571 | 5/1992 | Pier et al. | 210/143 |
| 5,120,450 | 6/1992 | Stanley, Jr. | 210/748 |
| 5,124,033 | 6/1992 | Ohmi et al. | 210/181 |
| 5,128,043 | 7/1992 | Wildermuth | 210/695 |
| 5,160,429 | 11/1992 | Ohmi et al. | 210/900 |
| 5,178,758 | 1/1993 | Hwang | 210/256 |
| 5,178,768 | 1/1993 | White, Jr. | 210/663 |
| 5,190,659 | 3/1993 | Wang et al. | 210/663 |
| 5,227,053 | 7/1993 | Brym | 210/748 |
| 5,238,581 | 8/1993 | Frame et al. | 210/763 |
| 5,259,972 | 11/1993 | Miyamaru et al. | 210/900 |

OTHER PUBLICATIONS

Article Entitled "Contaminated Water" *Wellness Lifestyle*, Jan. 1990.

*Primary Examiner*—Cynthia L. Nessler
*Attorney, Agent, or Firm*—Rhodes Coats & Bennett

[57] ABSTRACT

An apparatus for purifying water includes:

a plurality of UV radiators which include a helical quartz tube through which water to be purified passes and an ultraviolet light source to irradiate water passing through the helical quartz tube to remove microbes, a plurality of filtration stages including fine, ultra-fine and micro filters, a reactor including a bed of gold, and an irradiation stage including a quartz tube through which water to be purified passes and a laser light source with a wavelength in the range of 200–300 nm to irradiate water passing through the quartz tube, whereby microbes in the water passing through the apparatus are killed and removed.

18 Claims, 2 Drawing Sheets

WATER PURIFICATION SYSTEM

BACKGROUND OF THE INVENTION

The present invention relates to methods and apparatus for making highly purified water which is beneficial for human consumption.

Although water is a vital constituent in maintaining human life, all too often, modern water supplies, even after treatment in municipal plants, are loaded with chemicals, viruses and bacteria. These impurities are present and are not conventionally thought of as harmful or disease-causing. However, the constant bombardment of the human organism and its sensitive immune system with these impurities through the consumption of water tainted with these impurities, over time, can have deleterious effects on human health.

Various attempts have been made in the past to provide water purification, including the plethora of devices and designs incorporated into municipal water treatment systems. However, none of these designs achieve a high degree of purity in the resulting water. The continued consumption of such water continues to lead to the deleterious effects noted above.

Accordingly, there is a need in the art for an improved water treatment method and apparatus for obtaining highly pure water to aid in the human condition by reducing disease and other health problems.

SUMMARY OF THE INVENTION

The present invention fulfills this need by providing an apparatus for purifying water including the following components, connected in series:
  a first UV radiator to remove microbes including a helical quartz tube through which water to be purified passes and an ultraviolet light source to irradiate water passing through the helical quartz tube,
  a first filtration stage including a fine filter and an ultra-fine filter,
  a first reactor including a bed of coarse quartz granules, followed by a bed of noble metal,
  a second filtration stage including a fine filter and an ultra-fine filter,
  a second UV radiator to remove microbes including a helical quartz tube containing coarse quartz granules and through which water to be purified passes and an ultraviolet light source to irradiate water passing through the helical quartz tube,
  a second reactor including a bed of noble metal followed by a bed of coarse quartz granules,
  a third reactor including a bed of noble metal followed by a bed of coarse quartz granules,
  a fourth reactor including a bed of coarse quartz granules,
  a third filtration stage including a micro-filter,
  a fourth filtration stage including a micro-filter,
  a third UV radiator to remove microbes including a helical quartz tube through which water to be purified passes and an ultraviolet light source to irradiate water passing through the helical quartz tube,
  a fifth filtration stage including an ultrafilter,
  a fourth reactor including a bed of gold, and
  an irradiation stage including a quartz tube through which water to be purified passes and a laser light source with a wavelength in the range of 200-300 nm to irradiate water passing through the quartz tube,
  whereby microbes in the water passing through the apparatus are killed and removed.

In more general terms, the apparatus can be described as including a UV radiator to remove microbes including a helical quartz tube through which water to be purified passes and an ultraviolet light source to irradiate water passing through the helical quartz tube. A reactor follows, including a bed of coarse quartz granules and a bed of noble metal. A further reactor includes a bed of gold, and an irradiation stage includes a quartz tube through which water to be purified passes and a laser light source with a wavelength in the range of 200-300 nm to irradiate water passing through the quartz tube. These components work together so that microbes in the water passing through the apparatus are killed and removed.

Preferably, the apparatus includes a bottling facility for bottling the purified water in clean glass bottles including a source of ozone to blanket the interface between the purified water and atmosphere with ozone as water is being filled into the bottles.

In a less expensive form the apparatus includes a UV radiator to remove microbes including a quartz tube through which water to be purified passes and an ultraviolet light source to irradiate water passing through the quartz tube, a first filtration stage including a fine filter and an ultra-fine filter, a reactor including a bed of coarse quartz granules, followed by a bed of noble metal, and a second filtration stage including a fine filter and an ultra-fine filter. Although some purity is sacrificed, this arrangement also has the effect that microbes in the water passing through the apparatus are killed and removed.

The filters in the first filtration stage create a backpressure on the water in the UV radiator, which coupled with heating by the ultraviolet light source, results in oscillations in the water which are destructive to the microbes.

Preferably, the UV radiator is provided with airflow passages around the quartz tube, resulting in the formation of ozone, and tubing is provided to bubble the ozone through the water.

The noble metal may be selected from the group consisting of silver, gold, platinum, palladium, ruthenium, rhodium, iridium, and osmium.

Preferably, a second UV radiator is also provided including a quartz tube containing coarse quartz granules and through which water to be purified passes and an ultraviolet light source to irradiate water passing through the helical quartz tube, the coarse quartz granules being of high purity and a diameter of 0.25-1.0 min.

All surfaces with which the water being purified comes into contact should be either quartz, gold or very pure stainless steel.

In another less expensive form the apparatus includes, connected in series: a first reactor including a bed of coarse quartz granules, a first filtration stage including a micro-filter, a second filtration stage including a micro-filter, a UV radiator to remove microbes including a quartz tube through which water to be purified passes and an ultraviolet light source to irradiate water passing through the quartz tube, a third filtration stage including an ultrafilter, a second reactor including a bed of gold, and an irradiation stage including a quartz tube through which water to be purified passes and a laser light source with a wavelength in the range of 200–300 nm to irradiate water passing through the quartz tube.

The invention also provides a method of purifying water including passing the water through the following steps in series:
  removing microbes and photo-oxidizing chemicals in a helical quartz tube by irradiation of the water with ultraviolet light,
  filtering out microbes in a fine filter and an ultra-fine filter,
  exciting a bed of coarse quartz granules with heat from the ultraviolet light absorbed by the water so that the granules vibrate and destroy microbes, followed by sterilization of the water by exposure to a bed of noble metal,
  filtering out microbes in a fine filter and an ultra-fine filter,
  again removing microbes and photo-oxidizing chemicals in a helical quartz tube by irradiation of the water with ultraviolet light with coarse quartz granules in the tube,
  exciting another bed of coarse quartz granules with heat from the ultraviolet light absorbed by the water so that the granules vibrate and destroy microbes, followed by sterilization of the water by exposure to a bed of noble metal,
  exciting another bed of coarse quartz granules with heat from the ultraviolet light absorbed by the water so that the granules vibrate and destroy microbes,
  filtering out microbes in a micro-filter
  again removing microbes and photo-oxidizing chemicals in a helical quartz tube by irradiation of the water with ultraviolet light with coarse quartz granules in the tube,
  filtering out microbes in an ultrafilter,
  sterilizing the water by exposure to gold,
  irradiation the water with laser light with a wavelength in the range of 200–300 nm,
  whereby microbes in the water are killed and removed.

In a less expensive form the method includes passing the water through the following steps: removing microbes and photo-oxidizing chemicals in a helical quartz tube by irradiation of the water with ultraviolet light, exciting a bed of coarse quartz granules with heat from the ultraviolet light absorbed by the water so that the granules vibrate and destroy microbes, followed by sterilization of the water by exposure to a bed of noble metal, sterilizing the water by exposure to gold, and irradiation the water with laser light with a wavelength in the range of 200–300 nm, whereby microbes in the water are killed and removed.

Preferably, the method includes bottling the purified water in clean glass bottles while providing a blanket of ozone at the interface between the purified water and atmosphere as water is being filled into the bottles.

In another less expensive form, the method includes passing the water through the following steps in series: removing microbes and photo-oxidizing chemicals in a helical quartz tube by irradiation of the water with ultraviolet light, filtering out microbes in a fine filter and an ultra-fine filter, exciting a bed of coarse quartz granules with heat from the ultraviolet light absorbed by the water so that the granules vibrate and destroy microbes, followed by sterilization of the water by exposure to a bed of noble metal, filtering out microbes in a fine filter and an ultra-fine filter, whereby microbes in the water are killed and removed.

Preferably, the removing step includes passing air around the quartz tube, resulting in the formation of ozone, and bubbling the ozone through the water.

Typically, the first filtering step creates a back-pressure on the water in the removing step, and the water is heated in the removing step by the ultraviolet light source, resulting in oscillations in the water which are destructive to the microbes.

Desirably, the method includes a second removing step to remove microbes including passing the water through a quartz tube which contains coarse quartz granules of high purity and a diameter of 0.25–1.0 mm and irradiating the water with ultraviolet light, resulting in oscillations of the quartz granules in the water which are destructive to the microbes.

In another less expensive form the method includes passing the water through the following steps in series: passing the water through a bed of coarse quartz granules, filtering out microbes in a micro-filter, removing microbes and photo-oxidizing chemicals in a helical quartz tube by irradiation of the water with ultraviolet light with coarse quartz granules in the tube, filtering out microbes in an ultrafilter, sterilizing the water by exposure to gold, and irradiating the water with laser light with a wavelength in the range of 200–300 nm, whereby microbes in the water are killed and removed.

BRIEF DESCRIPTION OF THE DRAWINGS

The invention will be better understood by the reading of the detailed description of the preferred embodiment, along with a review of the drawings in which.

DETAILED DESCRIPTION OF THE PREFERRED EMBODIMENT

The present invention provides a method and apparatus for treating what is conventionally described as potable water to make it of a high degree of purity. The infeed water is preferably from a conventional municipal water supply and has gone through the conventional municipal water supply treatments, which may include various filtering and sedimentation steps. The origin of the water may be any desired source, such as a lake, a river, melting ice, desalinized sea water or collected rain water.

Figure 1:
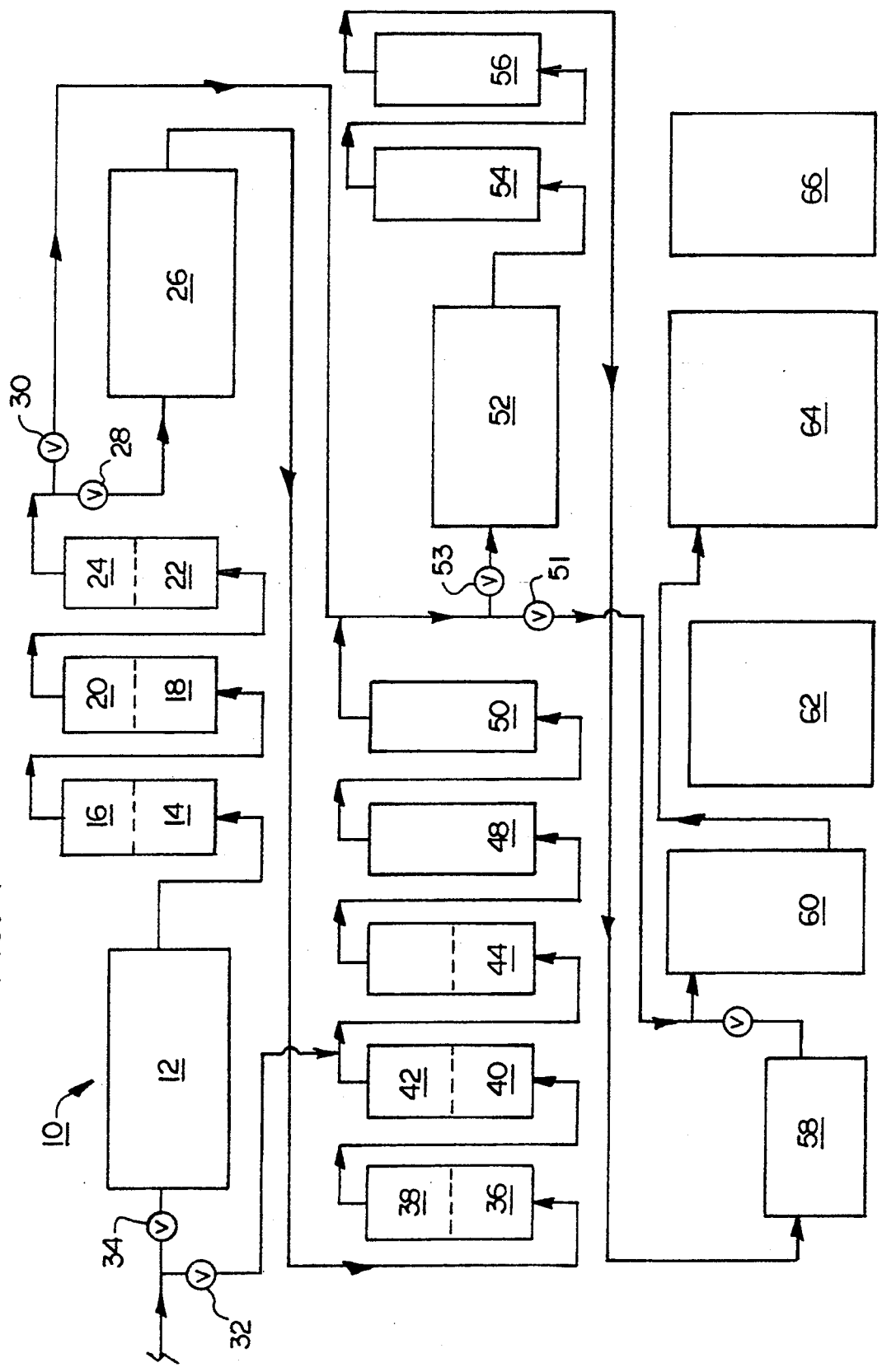
FIG. 1 is a block diagram of the various components used in a preferred embodiment, along with optional valve arrangements for less complete water treatment.

As seen in FIG. 1, the apparatus according to a preferred embodiment includes a number of modules thorough which the water is put, becoming all the more pure as it goes further through the system. Various ones of the components can be isolated and used separately through suitable activation of valves 32, 34, or valves 28, 30 or valves 51, 53. Preferably, the water is routed through all the components shown in FIG. 1 to achieve the highest degree of purity. As will be appreciated, routing thorough fewer components achieves some purification, but not as much as through all.

The following description will describe a thorough treatment of the water, passing through all of the components. As can be appreciated from a review of FIG. 1, fewer components may be used, such as by suitable activation of the above-mentioned valves.

Figure 2:
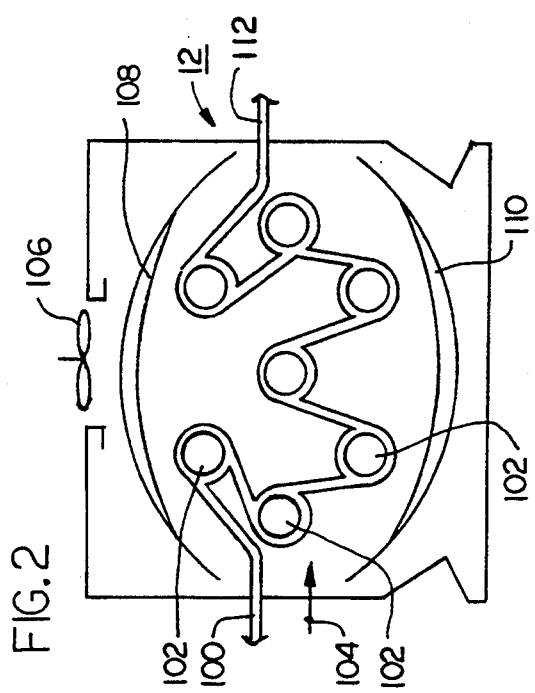
FIG. 2 is a sectional view through a UV radiator component used in the embodiment of FIG. 1.

The water is first introduced to a UV radiator 12 shown more clearly in FIG. 2 as a sectional view. The water is infeed through quartz tubing 100 which is directed to pass around a plurality of ultraviolet lamps 102. The transparent quartz tubing 100, of course, permits the ultraviolet light to pass through it, thus irradiating the water passing thorough the tubing. The quartz of the tubing needs to be of a very high purity. Mirrors 108 and 110 are provided to redirect ultraviolet light back to the quartz tubing in order to provide radiation as intense as possible. Preferably, the ultraviolet radiation is in the spectrum range of 180–300 nanometers and most preferably 254 nanometers. Also, preferably the UV lamps 102 are elongated and the quartz tubing spirals around the UV lamps in a helical fashion in order to maximize the period of time of the exposure of water passing through the quartz tubing to the ultraviolet light.

As an alternative, the water could be passed through straight tubes like tubes 102 with the ultraviolet light being emitted by a spirally wound tube like the tube 100. An arrow 104 indicates an air infeed path which is to provide cooling for the apparatus, under the influence of fan 106. The passage of the air through the intense ultraviolet light will cause the generation of ozone, which can be passed through the water to aid in purification. This is not shown in the drawings but may be done upstream in the municipal water system, or downstream of the UV radiator 12. From the UV radiator 12, the water is directed to a fine filter 14 and an ultra-fine filter 16.

After the ultra-fine filter 16, the water is passed through a reactor made up of stages 18 and 20. The lower portion 18 of the reactor is filled with coarse quartz granules, and the upper portion 20 is filled with noble metal balls. The balls are all of one noble metal, but may be any noble metal, including silver, gold, platinum, palladium, ruthenium, rhodium, iridium, and osmium. A preferred noble metal is silver. Preferably, the balls are provided with a lot of holes, providing a large surface area for intimate contact between the water and the noble metal. This provides a catalyst-like structure to maximum the effective area of the noble metal exposed to the water.

Figure 3:
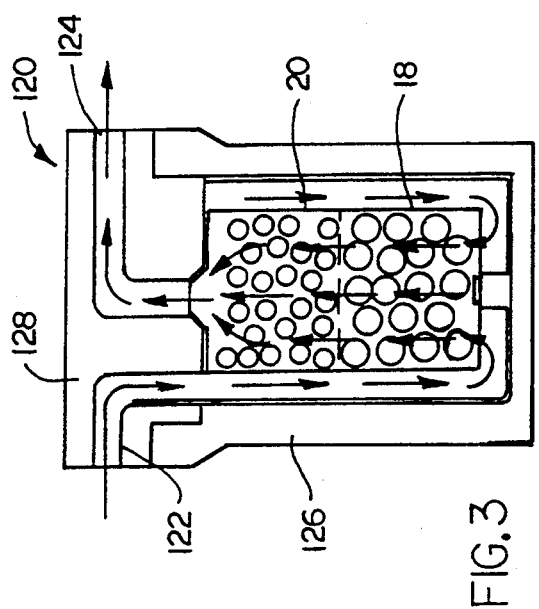
FIG. 3 is a sectional view through a reactor cartridge according to the embodiment of FIG. 1.

The two reactor bed stages 18 and 20 can be seen disposed in a canister arrangement in FIG. 3. The canister arrangement can be used for the various reactors shown in the drawing FIG. 1.

The canister 126 making up the reactor housing 120 mounts to a support 128 into which the water is introduced through an inlet 122. The inlet 122 leads to the bottom of the chamber 18 in which the quartz granules are disposed. Above the quartz granules 18 are the noble metal balls 20. From the top of the noble metal ball bed 20, the water exits through an exit 124. The provision of these components in a canister arrangement of this sort permits the cleaning or replacement of the quartz and/or noble metal balls, should that ever become necessary.

While the UV radiator itself is believed to kill perhaps some 20% of the microbes passing it thorough photo oxidation of the chemicals and the destruction of bacteria and virus, it also cooperates with the filter components 14 and 16. Pressure is created in the UV radiator by resistance from the filters and by expansion of the water from the heating inherent in the ultraviolet radiation. This can cause localized killing of the viruses and bacteria.

Furthermore, the downstream quartz granules in reactor 18 are provided in various sizes and purities to that the heat and pressure cause them to oscillate. This causes the emission of radiation that further destroys some viruses by penetrating membranes of the viruses.

The noble metal, particularly silver, in the reactor bed 20 has the property of a sterilizer. As the energized water from the quartz enters the silver bed, electrons in the silver travel faster and make additional radiation which can cause further viral destruction.

Downstream of the reactor beds 18 and 20 are further filter stages 22 and 24. The filter 22 is provided as a coarse filter with the filter 24 as a fine filter.

The water then passes into another UV radiator 26 which is much like the UV radiator 12, except that: the quartz tubing 100 is itself filled with quartz granules, so that the water passing through the tubing 100 of the UV radiator 26 is again in intimate contact with quartz granules. The ultraviolet light entering the tubing 100 of the UV radiator 26 causes the quartz granules to pulsate, to physically kill viruses and bacteria. The shapes of the granules of the quartz are not critical, but the preferably have a size range of 0.25 to 1.0 mm in diameter. Downstream of the UV radiator 26, the water passes through additional reactor bed 36 containing a noble metal, like the noble metal of the reactor bed 20 and into reactor bed 38, which contains quartz granules. From there, the water passes through a reactor bed 40 again having the noble metal and then into a reactor bed 42 having quartz granules. Next, the water is directed to a reactor 44 filled with only the quartz granules. Downstream of the reactor 44, the water passes thorough two microfiltration stages 48 and 50.

Downstream of the filter 50, the water passed through another UV radiator 52 identical in virtually all respects to the UV radiator 12.

Figure 4:
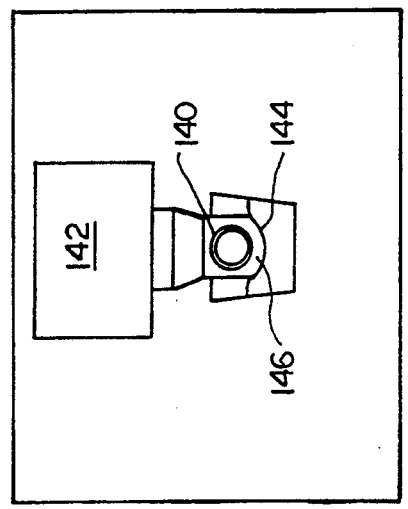
FIG. 4 is an enlarged side view of a laser radiation component according to the embodiment of FIG. 1.
Figure 5:
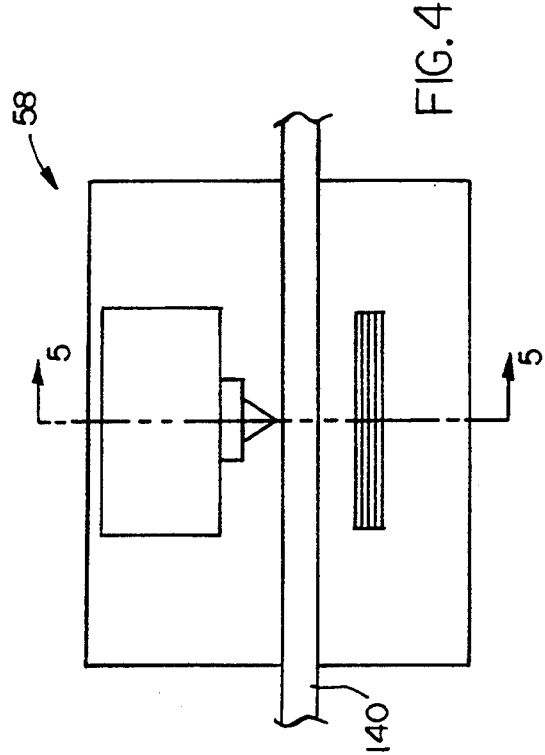
FIG. 5 is a sectional view of the laser radiation component of FIG. 4 taken along lines 5—5 and looking in the direction of the arrows.

The output of UV radiator 52 is then passed through ultra filter 54 and through a further reactor 56 filled with gold balls again having a catalyst-style surface. The gold "polishes" the water, providing more virus killing ability. The water passing from the reactor 56 is then passed through a laser irradiation component 58. This component can be better seen in FIGS. 4 and 5. The laser 142 preferably emits a wide beam of laser light of a wavelength in the range of 200–300 nanometers to fully cover the quartz tube 140 through which the water passes. A mirror 144 may be provided to further irradiate the water in the tube 140. An air flow 146 may again be provided for cooling the quartz tube. The resulting ozonated air may be passed through one of the earlier pretreatment stages, as discussed above. The water output of the laser irradiation component 58 is then applied to a storage tank 60.

A bottling preparation facility 62 may be provided in which the bottles that are to be stored and shipped are irradiated with ultraviolet light and ozone is supplied in place of air, to keep out contaminants. Preferably the bottles are quartz glass in order to prevent the leaching of contaminants into the water. Alternatively, a silver-lined, plastic bottle could be used or other leach-free glass. The water is supplied from the storage tank 60 for filling in the bottles from the supply 62 under a constant ultraviolet illumination and/or ozone in order to prevent recontamination.

The piping connecting the various components must be of character so as not to introduce contaminants such as by dissolving into the water. Thus, the piping and the storage tank 60 should be quartz, gold-plated or a very high grade of stainless steel. Also, it is desirable to fill the ullage of the tank 60 with ozone, such as the ozone generated by the laser 58.

The operation of the apparatus is straight-forward. The UV radiator 12 receives the infeed from municipal water supply and then passes the feed thorough the filter stages 14 and 16. From there it is passed through the reactors 18 and 20 and through the filters 22 and 24. Then, depending on the settings of the valves 28 and 30, the water may pass to UV radiator 26, reactors 36, 38, 40, 42 and 44 and filter stages 48 and 50. A lesser degree of purification can be obtained by closing valve 34 and opening valve 32 and directing the water from the municipal water supply directly to the reactor 44, bypassing the earlier elements.

Similarly, if the valve 28 has been closed and the valve 30 has been opened, the water will have bypassed the components from UV radiator 26 to the filter 50 and applied directly to UV radiator 52, if valve 53 is opened. If, instead, valve 53 is closed and valve 51 is open, the water would immediately go to storage 60. With the valve 53 open, the water passes through UV radiator 52, ultra filter 54 and gold bed 56 before passing to the laser irradiation component 58 and to storage 60.

When filters are part of the system, they are desirably changed occasionally.

While the use of the noble metals and gold may entail a high expenditure to establish the apparatus in the invention, the operating costs are very low.

Those of ordinary skill in the art will appreciate that various modifications can be made to the apparatus as specifically and still fall within the scope of the invention.

What is claimed is:

1. An apparatus for purifying water comprising, connected in the following series:
   a first UV radiator to remove microbes including a helical quartz tube through which water to be purified passes and an ultraviolet light source to irradiate water passing through said helical quartz tube, said helical quartz tube being wrapped around said source,
   a first filtration stage including a fine filter and an ultra-fine filter,
   a first reactor including a bed of coarse quartz granules, followed by a bed of noble metal,
   a second filtration stage including a fine filter and an ultra-fine filter,
   a second UV radiator to remove microbes including a helical quartz tube containing coarse quartz granules and through which water to be purified passes and an ultraviolet light source to irradiate water passing through said helical quartz tube, said helical quartz tube being wrapped around said source,
   a second reactor including a bed of noble metal followed by a bed of coarse quartz granules,
   a third reactor including a bed of noble metal followed by a bed of coarse quartz granules,
   a fourth reactor including a bed of coarse quartz granules,
   a third filtration stage including a micro-filter,
   a fourth filtration stage including a micro-filter,
   a third UV radiator to remove microbes including a helical quartz tube through which water to be purified passes and an ultraviolet light source to irradiate water passing through said helical quartz tube, said helical quartz tube being wrapped around said source,
   a fifth filtration stage including an ultrafilter,
   a fourth reactor including a bed of gold, and
   an irradiation stage including a quartz tube through which water to be purified passes and a laser light source with a wavelength in the range of 200–300 nm to irradiate water passing through said quartz tube,
   whereby microbes in the water passing through the apparatus are killed and removed.

2. An apparatus for purifying water comprising, connected in the following series:
   a UV radiator to remove microbes including a helical quartz tube through which water to be purified passes and an ultraviolet light source to irradiate water passing through said helical quartz tube, said helical quartz tube being wrapped around said source,
   a reactor including a bed of coarse quartz granules, followed by a bed of noble metal,
   a further reactor including a bed of gold, and
   an irradiation stage including a quartz tube through which water to be purified passes and a laser light source with a wavelength in the range of 200–300 nm to irradiate water passing through said quartz tube,
   whereby microbes in the water passing through the apparatus are killed and removed.

3. An apparatus as claimed in claim 2 further comprising a bottling means for bottling the purified water in clean glass bottles including a source of ozone to blanket the interface between the purified water and atmosphere with ozone as water is being filled into the bottles.

4. An apparatus for purifying water comprising, connected in the following series:
   a UV radiator to remove microbes including a helical quartz tube through which water to be purified passes and an ultraviolet light source to irradiate water passing through said quartz tube, said helical quartz tube being wrapped around said source,
   a first filtration stage including a fine filter and an ultra-fine filter,
   a reactor including a bed of coarse quartz granules, followed by a bed of noble metal, and
   a second filtration stage including a fine filter and an ultra-fine filter,
   whereby microbes in the water passing through the apparatus are killed and removed.

5. An apparatus as claimed in claim 4 wherein said UV radiator is provided with airflow passages around said quartz tube, resulting in the formation of ozone, and tubing is provided to bubble the ozone through the water.

6. An apparatus as claimed in claim 4 wherein the noble metal is selected from the group consisting of silver, gold, platinum, palladium, ruthenium, rhodium, iridium, and osmium.

7. An apparatus as claimed in claim 4 wherein the filters in said first filtration stage create a back-pressure on the water in said UV radiator, which coupled with heating by the ultraviolet light source, results in oscillations in the water which are destructive to the microbes.

8. An apparatus as claimed in claim 4 further comprising a second UV radiator to remove microbes including a helical quartz tube containing coarse quartz granules and through which water to be purified passes and an ultraviolet light source to irradiate water passing through said helical quartz tube, said helical quartz tube being wrapped around said source, said coarse quartz granules being of high purity and a diameter of 0.25–1.0 mm.

9. An apparatus as claimed in claim 4 wherein all surfaces with which the water being purified comes into contact are either quartz, gold or pure stainless steel.

10. An apparatus for purifying water comprising, connected in the following series:
    a first reactor including a bed of coarse quartz granules,
    a first filtration stage including a micro-filter,
    a second filtration stage including a micro-filter,
    a UV radiator to remove microbes including a helical quartz tube through which water to be purified passes and an ultraviolet light source to irradiate water passing through said quartz tube, said helical quartz tube being wrapped around said source,
    a third filtration stage including an ultrafilter,
    a second reactor including a bed of gold, and
    an irradiation stage including a quartz tube through which water to be purified passes and a laser light source with a wavelength in the range of 200–300 nm to irradiate water passing through said quartz tube,
    whereby microbes in the water passing through the apparatus are killed and removed.

11. A method of purifying water comprising passing the water through the following steps in series:
    removing microbes and photo-oxidizing chemicals in a helical quartz tube by irradiation of the water with ultraviolet light,
    filtering out microbes in a fine filter and an ultra-fine filter,
    exciting a bed of coarse quartz granules with heat from the ultraviolet light absorbed by the water so that the granules vibrate and destroy microbes, followed by sterilization of the water by exposure to a bed of noble metal,
    filtering out microbes in a fine filter and an ultra-fine filter,
    again removing microbes and photo-oxidizing chemicals in a helical quartz tube containing coarse quartz granules by irradiation of the water with ultraviolet light,
    exciting another bed of coarse quartz granules with heat from the ultraviolet light absorbed by the water so that the granules vibrate and destroy microbes, followed by sterilization of the water by exposure to a bed of noble metal,
    exciting another bed of coarse quartz granules with heat from the ultraviolet light absorbed by the water so that the granules vibrate and destroy microbes,
    filtering out microbes in a micro-filter
    again removing microbes and photo-oxidizing chemicals in a helical quartz tube by irradiation of the water with ultraviolet light with coarse quartz granules in the tube,
    filtering out microbes in an ultrafilter,
    sterilizing the water by exposure to gold,
    irradiating the water with laser light with a wavelength in the range of 200–300 nm,
    whereby microbes in the water are killed and removed.

12. A method of purifying water comprising passing the water through the following steps:
    removing microbes and photo-oxidizing chemicals in a helical quartz tube by irradiation of the water with ultraviolet light,
    exciting a bed of coarse quartz granules with heat from the ultraviolet light absorbed by the water so that the granules vibrate and destroy microbes, followed by sterilization of the water by exposure to a bed of noble metal,
    sterilizing the water by exposure to gold, and
    irradiating the water with laser light with a wavelength in the range of 200–300 nm,
    whereby microbes in the water are killed and removed.

13. A method as claimed in claim 12 further comprising bottling the purified water in clean glass bottles while providing a blanket of ozone at the interface between the purified water and atmosphere as water is being filled into the bottles.

14. A method of purifying water comprising passing the water through the following steps in series:
    removing microbes and photo-oxidizing chemicals in a helical quartz tube by irradiation of the water with ultraviolet light,
    filtering out microbes in a fine filter and an ultra-fine filter,
    exciting a bed of coarse quartz granules with heat from the ultraviolet light absorbed by the water so that the granules vibrate and destroy microbes, followed by sterilization of the water by exposure to a bed of noble metal,
    filtering out microbes in a fine filter and an ultra-fine filter,
    whereby microbes in the water are killed and removed.

15. A method as claimed in claim 14 wherein said removing step includes passing air around the quartz tube, resulting in the formation of ozone, and bubbling the ozone through the water.

16. A method as claimed in claim 14 wherein the first filtering step creates a back-pressure on the water in said removing step, and the water is heated in the removing step by the ultraviolet light source, resulting in oscillations in the water which are destructive to the microbes.

17. A method as claimed in claim 14 further comprising a second removing step to remove microbes including passing the water through a quartz tube which contains coarse quartz granules of high purity and a diameter of 0.25–1.0 mm and irradiating the water with ultraviolet light, resulting in oscillations of the quartz granules in the water which are destructive to the microbes.

18. A method of purifying water comprising, passing the water through the following steps in series:
    passing the water through a bed of coarse quartz granules,
    filtering out microbes in a micro-filter
    removing microbes and photo-oxidizing chemicals in a helical quartz tube containing coarse quartz granules by irradiation of the water with ultraviolet light,
    filtering out microbes in an ultrafilter,
    sterilizing the water by exposure to gold, and
    irradiating the water with laser light with a wavelength in the range of 200–300 nm,
    whereby microbes in the water are killed and removed.

* * * * *